US00PP32991P3

(12) United States Plant Patent
Clucas

(10) Patent No.: US PP32,991 P3
(45) Date of Patent: Apr. 20, 2021

(54) ***LOMANDRA* PLANT NAMED 'LM700'**

(50) Latin Name: ***Lomandra confertifolia* ssp. *rubiginosa***
Varietal Denomination: LM700

(71) Applicant: Evan Clucas, Mount Evelyn (AU)

(72) Inventor: Evan Clucas, Mount Evelyn (AU)

( * ) Notice: Subject to any disclaimer, the term of this patent is extended or adjusted under 35 U.S.C. 154(b) by 0 days.

(21) Appl. No.: 16/602,510

(22) Filed: Oct. 21, 2019

(65) Prior Publication Data

US 2020/0128716 P1 Apr. 23, 2020

Related U.S. Application Data

(60) Provisional application No. 62/748,716, filed on Oct. 22, 2018.

(51) Int. Cl.
*A01H 5/12* (2018.01)
*A01H 6/12* (2018.01)
*A01H 6/46* (2018.01)

(52) U.S. Cl.
USPC ..... Plt./373
CPC ..... *A01H 6/12* (2018.05); *A01H 6/46* (2018.05)

(58) Field of Classification Search
USPC ..... Plt./373, 384
CPC ..... A01H 5/02; A01H 5/00; A01H 5/12
See application file for complete search history.

*Primary Examiner* — Kent L Bell
(74) *Attorney, Agent, or Firm* — Samuel R. McCoy, Jr.

(57) ABSTRACT

'LM700' is a distinctive *Lomandra confertifolia* ssp. *rubiginosa* plant which is characterized by the combination of a short plant height, a weeping growth habit and fine-textured, greyed-green foliage. The new variety propagates successfully by division and tissue culture and has shown to be uniform and stable in the resulting generations from asexual propagation.

3 Drawing Sheets

Latin name of the genus and species: The Latin name of the genus and species of the novel variety disclosed herein is *Lomandra confertifolia* ssp. *rubiginosa.*

Variety denomination: The inventive variety of *Lomandra* disclosed herein has been given the variety denomination 'LM700'.

BACKGROUND OF THE INVENTION

Parentage: 'LM700' is the product of a seedling selection process carried out by the inventor at a commercial plant nursery in Mount Evelyn, Victoria, Australia from the year 2000 until 2015. The exact parentage of the claimed plant is unknown. In the spring of 2000, seeds harvested from a plurality of openly-pollinated *Lomandra confertifolia* ssp. *rubiginosa* plants were germinated, resulting in approximately 8,000 seedlings. These seedlings were grown to a mature size in nursery containers and subsequently evaluated from 2000 to 2008 in an effort to identify seedlings which exhibited a combination of improved vigor and unique growth characteristics which may be of commercial importance. In 2008, the seedlings which exhibited the above combination of characteristics were planted into the ground, at the same nursery location, for further evaluation. In 2015, one of these plants was selected for commercialization due to its clean, healthy foliage and improved plant density compared to all other progeny, other commercial comparators known to the Inventor, and the exemplary phenotype of the species. This new and distinctive cultivar was given the name 'LM700'.

Asexual Reproduction: 'LM700' was first asexually propagated in early 2015 by division of the plant's crown in Mount Evelyn, Victoria, Australia and has since been asexually reproduced by meristematic tissue culture propagation. The distinctive characteristics of the inventive 'LM700' variety have proven to be stable through five generations and plants so produced maintain the distinguishing characteristics of the original plant.

SUMMARY OF THE INVENTION

The following traits have been repeatedly observed and represent the characteristics of the new cultivar. These characteristics, in combination, distinguish 'LM700' as a distinct cultivar of *Lomandra:*

1. 'LM700' exhibits improved plant vigor and disease resistance when compared to similar cultivars of the same species; and
2. 'LM700' exhibits a short plant height with a dense tussock of arching foliage; and
3. 'LM700' exhibits fine-textured, greyed-green foliage.

BOTANICAL DESCRIPTION OF THE PLANT

Figure 1:
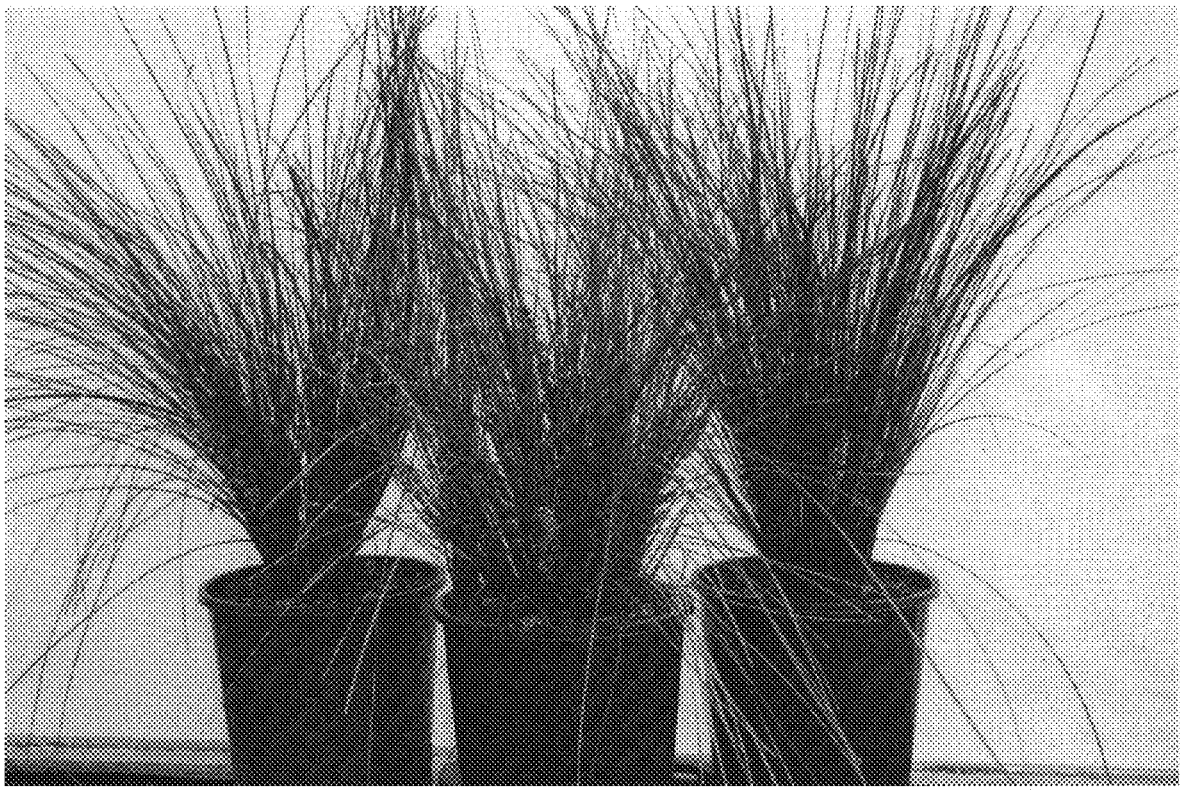
FIG. 1 illustrates, as true as is reasonably possible to obtain in color photographs of this type, exemplary 'LM700' specimens at approximately 12 months of age in a 140 mm (approximate) nursery pot, grown in Clarendon, NSW, Australia.
Figure 2:
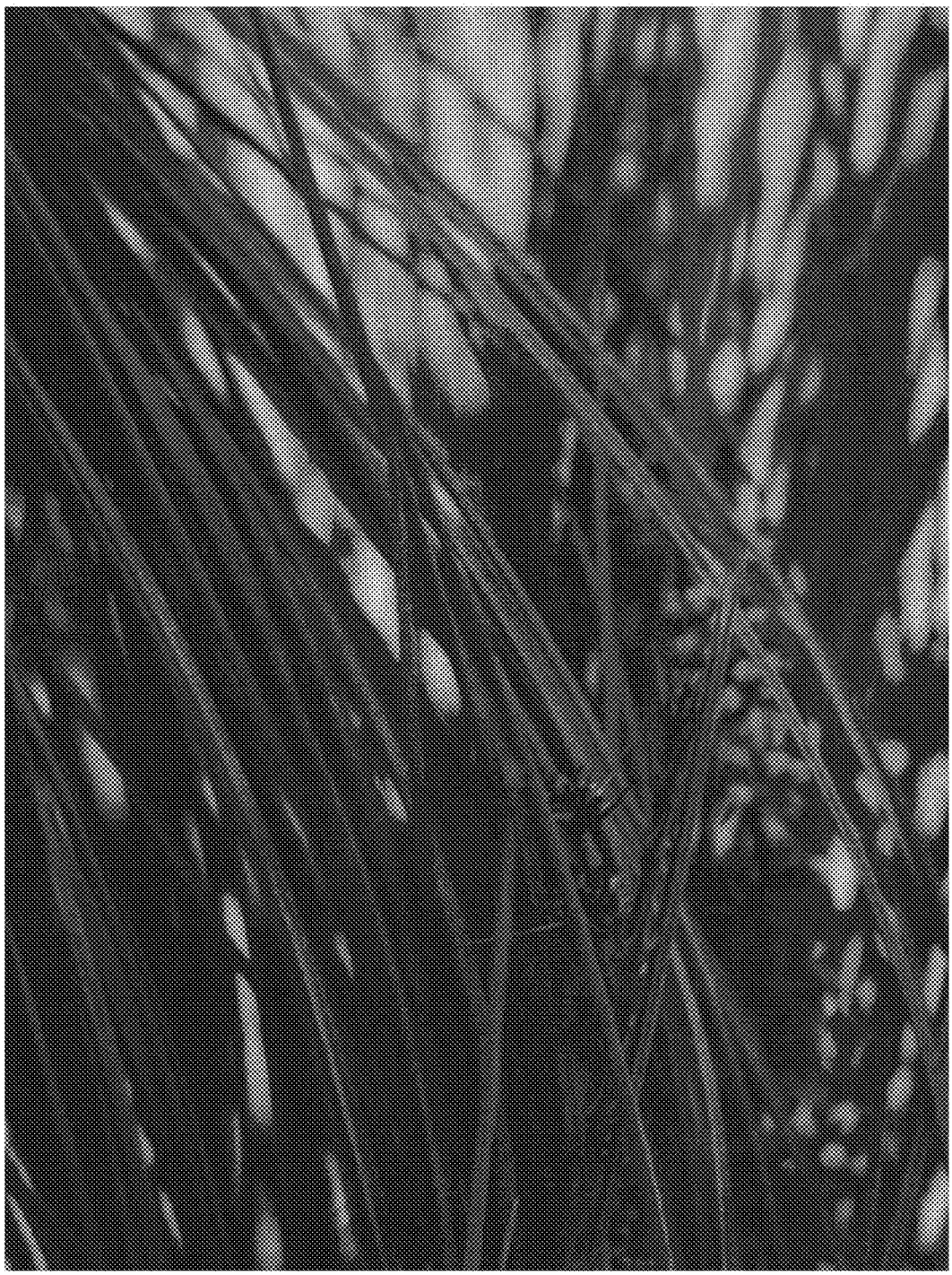
FIG. 2 illustrates, as nearly true as it is reasonably possible to make the same in color photographs of this type, the typical foliage of 'LM700'.
Figure 3:
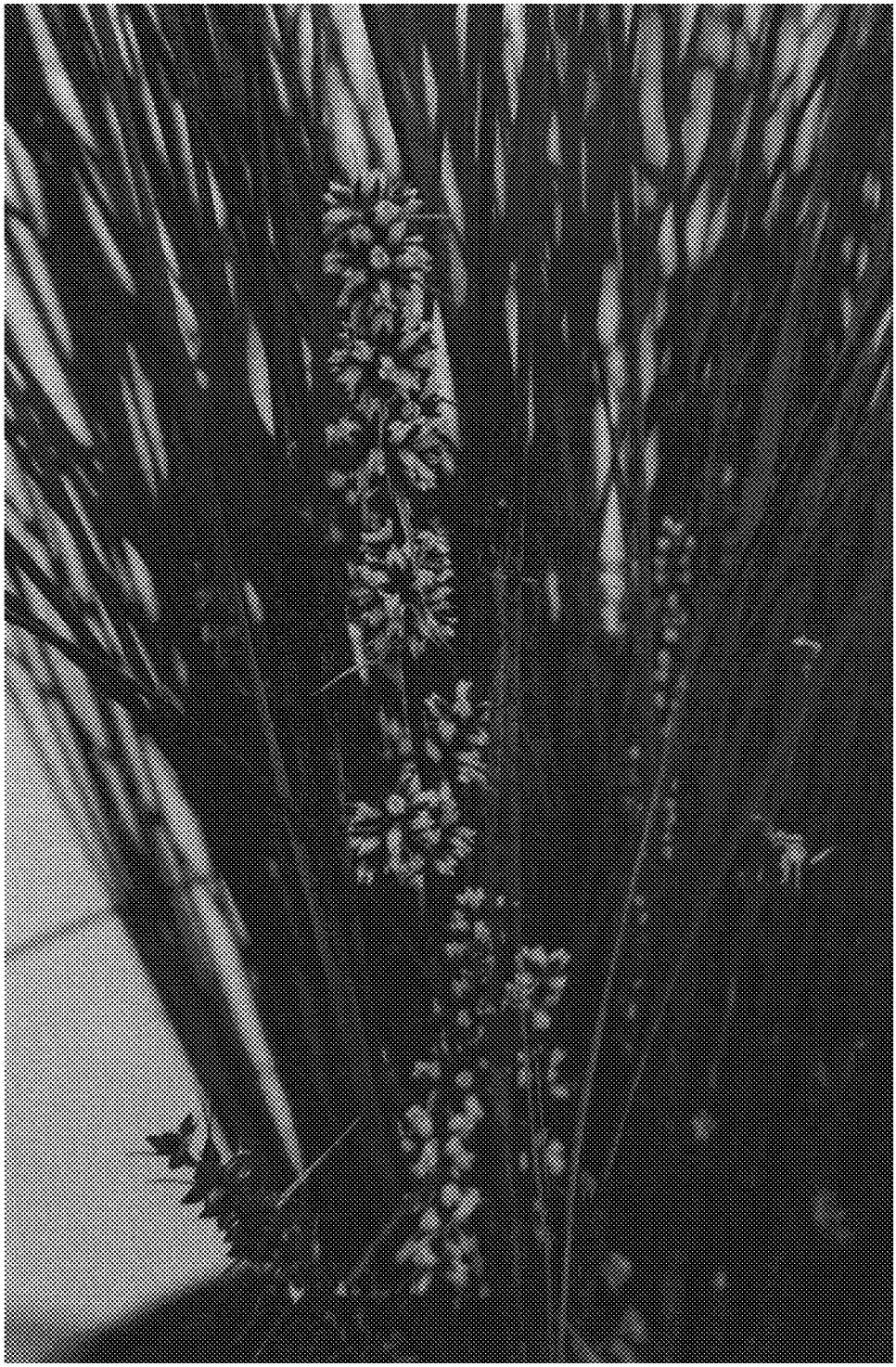
FIG. 3 illustrates, as nearly true as it is reasonably possible to make the same in color photographs of this type, the typical inflorescence of 'LM700'.

The following is a detailed botanical description of a new and distinct variety of a *Lomandra* ornamental plant known as 'LM700'. Plant observations were made on plants grown in Clarendon, NSW, Australia. Unless indicated otherwise, the descriptions disclosed herein are based upon observations made in October 2017 of 24 month old 'LM700' plants grown outdoors, in full sun, from rooted cuttings in 140 mm nursery pots filled with soilless potting media, maintained with granular slow release fertilizer and regularly watered with overhead irrigation. No pest and disease measures were taken.

Those skilled in the art will appreciate that certain characteristics will vary with older or, conversely, younger plants. 'LM700' has not been observed under all possible environmental conditions. Where dimensions, sizes, colors and other characteristics are given, it is to be understood that such characteristics are approximations or averages set forth as accurately as practicable. The phenotype of the variety may vary with variations in the environment such as season, temperature, light intensity, day length, cultural conditions and the like. Color notations are based on *The Royal Horticultural Society Colour Chart*, The Royal Horticultural Society, London, 2001 edition.

A botanical description of 'LM700' and comparisons with similar varieties of common knowledge are provided below.

General plant description:

*Plant habit*.—Grass-like perennial with arched foliage; rhizomatous plant forming a dense tussock.

*Reproduction*.—Dioecious; male of the species.

*Height*.—Approximately 40 cm at 5 years old.

*Width*.—Approximately 75 cm at 5 years old.

*Bloom period*.—Spring into summer in Victoria, Australia.

*Hardiness*.—USDA Zone 8 to 11.

*Propagation*.—Propagation is accomplished by dividing the crown of the plant and also by way of meristematic tissue culture propagation.

*Crop time*.—Time to develop a rooted cutting is approximately 10 to 12 weeks, from division. An average crop time is approximately 6 to 9 months to produce a mature and marketable 1-gallon nursery container, beginning with a rooted cutting.

*Environmental tolerances*.—Shade and drought tolerant.

*Pest and disease susceptibility or resistance*.—Improved resistance to *Fusarium* sp. and *Rhizoctonia* sp. root rotting diseases.

Roots: Densely rooting; roots are fibrous and distributed evenly throughout the soil profile, from shallow to deep.

Rhizomes:

*Length*.—4.25 cm.

*Diameter*.—0.65 cm.

*Texture*.—Smooth; glabrous.

*Color*.—White, nearest to RHS 155D.

Culm:

*Length*.—Ranging from 1.5 cm to 3.0 cm.

*Texture*.—Smooth; glabrous.

*Color*.—White, nearest to RHS 155C.

Foliage:

*Foliage density*.—Very dense.

*Arrangement*.—Distichous.

*Division*.—Simple.

*Attachment*.—Sheathed.

*Attitude*.—Proximal two-thirds portion of the leaf is semi-erect; distal one-third portion of the leaf is drooping.

*Aspect*.—Concaved; involute.

*Shape*.—Linear; grass-like.

*Apex*.—Tridentate. The leaf apex may become locally necrotic in response to moisture stress.

*Base*.—Sheathed attachment to the culm.

*Basal sheath*.—Greyed-purple, nearest to RHS 187A; margins tattered; apex is acute.

*Margins*.—Entire.

*Mature leaf dimensions*.—1.5 mm wide and 330 mm long, and 0.75 mm thick.

*Texture and luster, adaxial surface*.—Glabrous; smooth; matte and moderately glaucous.

*Texture and luster, abaxial surface*.—Glabrous; smooth; matte and lightly glaucous.

*Juvenile foliage color, adaxial & abaxial surfaces*.—Green, nearest to N138B.

*Mature foliage color, adaxial & abaxial surfaces*.—Green, nearest to N138B.

*Venation*.—Parallel.

*Vein color, adaxial surfaces*.—Green, nearest to N138B.

*Vein color, abaxial surfaces*.—Green, nearest to N138B.

Inflorescence:

*Type*.—Panicle containing small clusters of male flowers; flowers are sessile and whorled around the peduncle.

*Natural flowering season*.—Spring into early summer.

*Position*.—Racemes positioned at or slightly below the foliar plane.

*Overall dimensions*.—Up to 80 mm long, including the peduncle and rachis.

*Bloom habit*.—Very floriferous; inflorescences may potentially arise from every shoot.

*Peduncle*.—Dimensions — Up to 55 mm long and 2 mm in diameter. Attitude — Erect. Strength — Strong. Texture — Smooth. Color — Yellow-green, RHS 147A and very heavily suffused with black, RHS 202A.

Bud:

*Dimensions*.—Approximately 2 mm long and 1 mm wide.

*Bud shape*.—Ovate.

*Bud color*.—Yellow, RHS 13A.

*Rate of bud opening*.—Slow.

Flower:

*Quantity*.—Approximately 40 flowers per inflorescence.

*Shape*.—Cupuliform; cup-shaped.

*Persistence*.—Non-persistent.

*Lastingness*.—Approximately 5 days.

*Aspect*.—Semi-erect to outward.

*Fragrance*.—Moderately fragrant; sweet perfume.

*Perianth*.—Calyx — Shape — Ovate. Diameter — Approximately 1 mm. Sepals — Arrangement — Alternate. Quantity — Three. Margin — Entire. Apex — Aristate. Base — Truncate. Texture — Smooth. Sepal color, immature, upper surface — Nearest to in between greyed-purple, RHS 187A, and black, RHS 202A. Sepal color, immature, under surface — Nearest to in between greyed-purple, RHS 187A, and black, RHS 202A. Sepal color, mature, upper surface — Nearest to in between greyed-purple, RHS 187A, and black, RHS 202A. Sepal color, mature, under surface — Nearest to in between greyed-purple, RHS 187A, and black, RHS 202A. Corolla — Arrangement — Alternate; petals unfused. Dimensions — Approximately 2 mm in diameter and 4 mm deep. Petals — Quantity — Three. Arrangement — Alternate. Dimensions — Approximately 1.5 mm long and 1.0 mm wide. Shape — Ovate. Margin — Entire. Apex — Acute. Base — Obtuse. Texture — Smooth. Color when opening, upper side — Yellow, nearest to RHS 13B. Color when opening, under side — Yellow, nearest to RHS 13B. Color when fully opened, upper side — Yellow, nearest to RHS 13B. Color when fully opened, under side — Yellow, nearest to RHS 13B. Bracts — Shape — Needle-shaped. Length — Varying from 6 to 9 mm. Width — 2.5 mm. Apex — Acute. Margin — Entire. Texture — Smooth. Color — Greyed-yellow, nearest to RHS 160D. Pedicels — Length — 0.8 cm. Diameter — 1.25 mm in diameter. Strength — Moderately strong. Texture — Smooth. Color — Yellow-green, nearest to a mixture of RHS 145A and 145B.

Reproduction organs: Not observed.

Seed: Flowers are male; seed is not produced.

COMPARISONS WITH THE MOST SIMILAR VARIETIES OF COMMON KNOWLEDGE

Plants of the new cultivar 'LM700' may be distinguished from the exemplary phenotype of *Lomandra confertifolia* ssp. *rubiginosa*, which would be representative of the parentage, by following characteristics described in Table 1 below.

TABLE 1

| Characteristic | 'LM700' | *Lomandra con fertifolia* ssp. *rubiginosa* |
|---|---|---|
| Plant vigor. | More vigorous; longer-lived in the landscape. | Less vigorous; shorter-lived in the landscape. |
| Foliage density. | More densely foliaged. | Less densely foliaged. |
| Leaf width. | Narrower than *Lomandra confertifolia* ssp. *rubiginosa* | Wider than 'LM700'. |
| General coloration of the foliage, epicuticular wax (glaucosity) removed. | Green. | Yellow-green. |

Plants of the new cultivar 'LM700' may be distinguished from the commercial variety, *Lomandra* sp. 'Seascape' (U.S. Plant Pat. No. 20,010), in the following characteristics described in Table 2 below.

TABLE 2

| Characteristic | 'LM700' | 'Seascape' |
|---|---|---|
| Plant vigor. | More vigorous; longer-lived in the landscape. | Less vigorous; shorter-lived in the landscape. |
| Foliage density. | More densely foliaged. | Less densely foliaged. |
| Growth habit. | Arched. | Weeping. |
| Leaf width. | Narrower than 'Seascape'. | Wider than LM700'. |
| General coloration of the foliage, epicuticular wax (glaucosity) removed. | Green. | Yellow-green. |

That which is claimed is:

1. A new and distinct variety of *Lomandra confertifolia* ssp. *rubiginosa* plant named 'LM700', substantially as described and illustrated herein.

* * * * *